United States Patent [19]

Regel et al.

[11] Patent Number: 4,729,783
[45] Date of Patent: Mar. 8, 1988

[54] HALOGENATED TRIAZOLYLVINYL KETO AND CARBINOL COMPOUNDS AND PLANT GROWTH REGULANT AND FUNGICIDAL COMPOSITIONS

[75] Inventors: Erik Regel, Wuppertal; Karl H. Büchel, Burscheid; Klaus Lürssen, Berg.-Gladbach; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 715,574

[22] Filed: Mar. 22, 1985

Related U.S. Application Data

[63] Continuation of Ser. No. 542,909, Oct. 18, 1983, abandoned, which is a continuation of Ser. No. 276,842, Jun. 24, 1981, abandoned.

[30] Foreign Application Priority Data

Jul. 3, 1980 [DE] Fed. Rep. of Germany ....... 3025242
Mar. 20, 1981 [DE] Fed. Rep. of Germany ....... 3111012

[51] Int. Cl.$^4$ ............... A01N 43/653; A61K 31/41; C07D 249/08
[52] U.S. Cl. ......................................... 71/92; 71/76; 514/383; 548/262
[58] Field of Search ............. 71/76, 92; 548/262; 514/383

[56] References Cited

U.S. PATENT DOCUMENTS

| | | | |
|---|---|---|---|
| 4,005,083 | 1/1977 | Buchel et al. | 514/383 |
| 4,203,995 | 5/1980 | Funaki et al. | 548/262 |
| 4,255,434 | 3/1981 | Kramer et al. | 514/383 |
| 4,486,218 | 12/1984 | Reiser et al. | 514/383 |
| 4,500,537 | 2/1985 | Elbe et al. | 514/383 |

FOREIGN PATENT DOCUMENTS 0130661 11/1978 Japan ............................ 514/383

OTHER PUBLICATIONS

Burger, Medicinal Chemistry (New York, 1960), 2nd Ed., p. 1055, Rs. 403B8.

*Primary Examiner*—Glennon H. Hollrah
*Assistant Examiner*—D. L. Dinner
*Attorney, Agent, or Firm*—Felfe & Lynch

[57] ABSTRACT

Halogenated triazolylvinyl keto derivatives and carbinol derivatives of the general formula

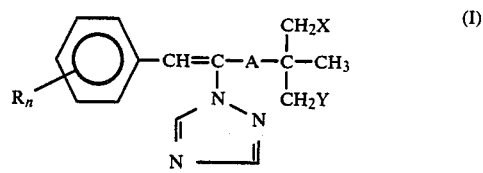

in which
  A represents a keto group or a CH(OH) grouping,
  X represents a hydrogen or halogen atom,
  Y represents a halogen atom,
  R represents a halogen atom, an alkyl, halogenoalkyl, halogenoalkoxy, alkoxy, alkylthio, halogenoalkylthio, alkylamino, dialkylamino, nitro, cyano, hydroxyl or alkylcarbonyloxy radical, an optionally substituted phenyl radical, an optionally substituted phenoxy radical or an optionally substituted benzyloxy radical and
  n is 0, 1, 2 or 3, and physiologically acceptable acid addition salts and metal salt complexes thereof are outstandingly effective as plant growth regulators and as fungicides. The inventive compounds can be prepared by reacting a triazolylketone with an aldehyde.

20 Claims, No Drawings

HALOGENATED TRIAZOLYLVINYL KETO AND CARBINOL COMPOUNDS AND PLANT GROWTH REGULANT AND FUNGICIDAL COMPOSITIONS

This application is a continuation, of application Ser. No. 542,909, filed Oct. 18, 1983, which is a continuation of Ser. No. 276,842, filed June 24, 1981, both abandoned.

This invention relates to certain new halogenated triazolylvinyl keto compounds and carbinol compounds. In further aspect the invention relates to a process for their production and their use in compositions, and to methods for regulating plant growth and as fungicides.

It is known that certain 4,4-dimethyl-1-phenyl-2-triazolyl-penten-3-ones and -ols have a good fungicidal activity (see Japanese Patent Application No. J5 3130 661 and DE-OS (German Published Specification) No. 2,838,847). However, the action f these compounds is not always completely satisfactory, especially when low amounts and low concentrations were applied. The plant growth-regulating action of these azole derivatives was likewise not always completely satisfactory.

The present invention now provides, as new compounds the halogenated triazolylvinyl keto derivatives and carbinol derivatives of the general formula

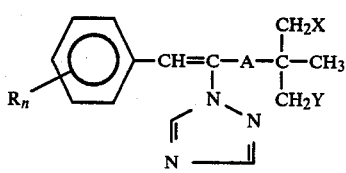

in which
A represents a keto group or a CH(OH) grouping,
X represents a hydrogen or halogen atom,
Y represents a halogen atom,
R represents a halogen atom, an alkyl, halogenoalkyl, halogenoalkoxy, alkoxy, alkylthio, halogenoalkylthio, alkylamino, dialkylamino, nitro, cyano, hydroxyl or alkylcarbonyloxy radical, an optionally substituted phenyl radical, an optionally substituted phenoxy radical or an optionally substituted benzyloxy radical and
n is 0, 1, 2 or 3, and physiologically acceptable acid addition salts and metal salt complexes thereof.

The compounds of the formula (I) according to the invention occur in the form of the geometric isomers E (trans) and Z (cis). In the E/Z nomenclature, the substituents on the double bond are arranged in order of decreasing priority in accordance with the Cahn-Ingold-Prelog rule. If the preferred substituents are on the same side of the double bond, the Z (derived from "zusammen" (together)) configuration is present, and if they are on opposite sides, the E (derived from "entgegen" (opposite)) configuration is present. If A represents the CH(OH) grouping, an asymmetric carbon atom is present, so that, in this case, the compound of the formula (I) are also obtained in two optical isomer forms. The present invention relates both to the individual isomers and the isomer mixtures.

According to the present invention there is further provided a process for the production of a compound of the present invention, characterised in that a triazolylketone of the general formula

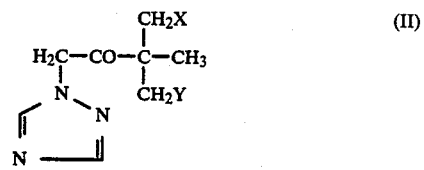

in which X and Y have the abovementioned meaning, is reacted with an aldehyde of the general formula

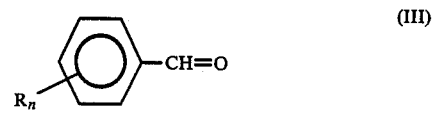

in which R and n have the abovementioned meaning, in the presence of a solvent and in the presence of a catalyst, and, if a compound of formula (I) is required in which A denotes the CH(OH) grouping, the halogenated triazolyl-vinyl keto derivative of the general formula

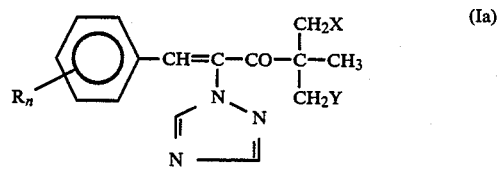

in which
X, Y, R and n have the abovementioned meaning, is then reduced;
and the resulting compound of the formula (I), in which A has either of its meanings, is then converted, if desired, into an acid addition salt or metal salt complex thereof.

Finally, it has been found that the new halogenated triazolylvinyl keto derivatives and carbinol derivatives of the formula (I) and acid addition salts and metal salt complexes thereof have powerful plant growth-regulating properties and powerful fungicidal properties.

Surprisingly, the compound of the present invention exhibit a better fungicidal and growth-regulating action than the 4,4-dimethyl-1-phenyl-2-triazolyl-1-penten-3-ones and -ols which are known from the state of the art and are closely related compounds chemically and from the point of view of their action. The active compounds according to the invention thus represent an enrichment of the art.

Preferred halogenated triazolylvinyl keto derivatives and carbinol derivatives according to the present invention are those in which X represents a hydrogen, fluorine, chlorine or bromine atom, Y represents a fluorine, chlorine or bromine atom, R represents a fluorine, chlorine or bromine atom, a straight-chain or branched alkyl, alkoxy or alkylthio radical with in each case 1 to 4 carbon atoms; a halogenoalkyl, halogenoalkoxy or halogenoalkylthio radical with in each case 1 or 2 carbon atoms and up to 5 identical or different halogen atoms (such as, preferably, fluorine and chlorine atoms); an alkylamino or dialkylamino radical with in each case 1 to 2 carbon atoms in each alkyl part); a nitro, cyano or hydroxyl radical, an alkylcarbonyloxy radical with 1 to 4 carbon atoms in the alkyl part; or an optionally substituted phenyl, phenoxy or benzyloxy radical, (preferred substituents which may be mentioned being: fluorine, chlorine, bromine and alkyl with 1 or 2 carbon atoms), and A and n have the abovementioned meanings.

Particularly preferred compounds of the present invention are those in which X represents a hydrogen atom and Y represents a fluorine or chlorine atom, or X and Y are identical and represent fluorine or chlorine atoms; R represents a fluorine or chlorine atom, a methyl, isopropyl, tert.-butyl, methoxy, methylthio, isopropoxy, trifluoromethyl, difluorochloromethyl, fluorodichloromethyl, trichloromethyl, 1,1,2-trifluoro-2-chloro-ethyl, trifluoromethoxy, trifluoromethylthio, 1,1,2-trifluoro-2-chloroethoxy and -ethylthio, dimethylamino, nitro, cyano, hydroxyl, acetoxy or tert.-butylcarbonyloxy radical, or a phenyl, phenoxy or benzyloxy radical which is optionally monosubstituted or disubstituted by identical or different substituents selected from fluorine, chlorine and/or methyl; and A and n have the abovementioned meanings.

The following compounds of the general formula (I) may be mentioned specifically, in addition to the compounds mentioned in the Preparative Examples:

TABLE 1

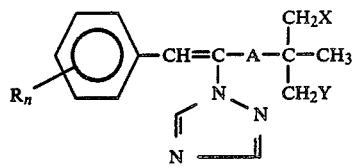
(I)

| $R_n$ | A | X | Y |
|---|---|---|---|
| 4-Cl | CO | Cl | Cl |
| 4-Cl | CH(OH) | Cl | Cl |
| 4-C(CH₃)₃ | CO | Cl | Cl |
| 4-C(CH₃)₃ | CH(OH) | Cl | Cl |
| 2,4-Cl₂ | CO | Cl | Cl |
| 2,4-Cl₂ | CH(OH) | Cl | Cl |
| 2-Cl | CO | Cl | Cl |
| 2-Cl | CH(OH) | Cl | Cl |
| 4-Cl | CO | F | F |
| 4-Cl | CH(OH) | F | F |
| 4-C(CH₃)₃ | CO | F | F |
| 4-C(CH₃)₃ | CH(OH) | F | F |
| 2,4-Cl₂ | CO | F | F |
| 2,4-Cl₂ | CH(OH) | F | F |
| 2-Cl | CO | F | F |
| 2-Cl | CH(OH) | F | F |
| 4-CF₃ | CO | H | Cl |
| 2-CF₃ | CO | H | Cl |
| 2-Cl,4-CF₃ | CO | H | Cl |
| 4-OCH₃ | CO | H | Cl |
| 4-SCH₃ | CO | H | Cl |
| 4-OH | CO | H | Cl |
| 2-OH,3,5-Cl₂ | CO | H | Cl |
| 4-NO₂ | CO | H | Cl |
| 4-OH,3-OCH₃ | CO | H | Cl |
| 4-phenyl | CO | H | Cl |
| 4-(4-Cl-phenyl) | CO | H | Cl |

TABLE 1-continued

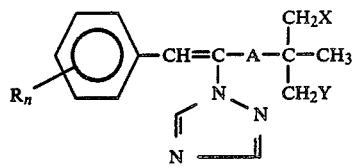
(I)

| $R_n$ | A | X | Y |
|---|---|---|---|
| 4-O-phenyl | CO | H | Cl |
| 4-O-(4-Cl-phenyl) | CO | H | Cl |
| 4-O-CH₂-phenyl | CO | H | Cl |
| 4-O-CH₂-(4-Cl-phenyl) | CO | H | Cl |
| 4-CF₃ | CH(OH) | H | Cl |
| 2-CF₃ | CH(OH) | H | Cl |
| 2-Cl,4-CF₃ | CH(OH) | H | Cl |
| 4-OCH₃ | CH(OH) | H | Cl |
| 4-SCH₃ | CH(OH) | H | Cl |
| 4-OH | CH(OH) | H | Cl |
| 2-OH,3,5-Cl₂ | CH(OH) | H | Cl |
| 4-NO₂ | CH(OH) | H | Cl |
| 4-OH,3-OCH₃ | CH(OH) | H | Cl |
| 4-phenyl | CH(OH) | H | Cl |
| 4-(4-Cl-phenyl) | CH(OH) | H | Cl |
| 4-O-phenyl | CH(OH) | H | Cl |
| 4-O-(4-Cl-phenyl) | CH(OH) | H | Cl |
| 4-O-CH₂-phenyl | CH(OH) | H | Cl |
| 4-O-CH₂-(4-Cl-phenyl) | CH(OH) | H | Cl |
| 4-CF₃ | CO | H | F |
| 2-CF₃ | CO | H | F |
| 2-Cl,4-CF₃ | CO | H | F |

TABLE 1-continued

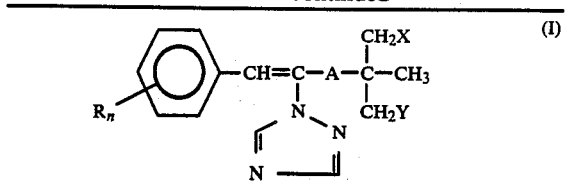

| $R_n$ | A | X | Y |
|---|---|---|---|
| 4-OCH$_3$ | CO | H | F |
| 4-SCH$_3$ | CO | H | F |
| 4-OH | CO | H | F |
| 2-OH,3,5-Cl$_2$ | CO | H | F |
| 4-NO$_2$ | CO | H | F |
| 4-OH,3-OCH$_3$ | CO | H | F |
| 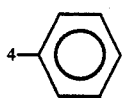 | CO | H | F |
| 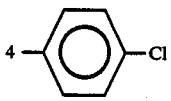 | CO | H | F |
| 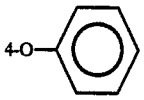 | CO | H | F |
| 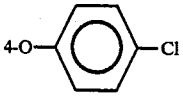 | CO | H | F |
| 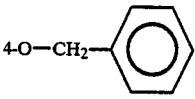 | CO | H | F |
| 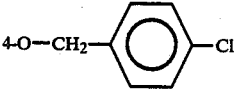 | CO | H | F |
| 4-CF$_3$ | CH(OH) | H | F |
| 2-CF$_3$ | CH(OH) | H | F |
| 2-Cl,4-CF$_3$ | CH(OH) | H | F |
| 4-OCH$_3$ | CH(OH) | H | F |
| 4-SCH$_3$ | CH(OH) | H | F |
| 4-OH | CH(OH) | H | F |
| 2-OH,3,5-Cl$_2$ | CH(OH) | H | F |
| 4-NO$_2$ | CH(OH) | H | F |
| 4-OH,3-OCH$_3$ | CH(OH) | H | F |
| 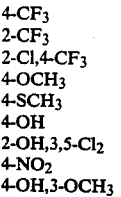 | CH(OH) | H | F |
| 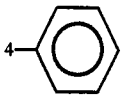 | CH(OH) | H | F |
| 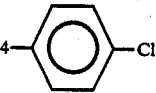 | CH(OH) | H | F |
| 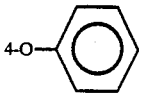 | CH(OH) | H | F |

TABLE 1-continued

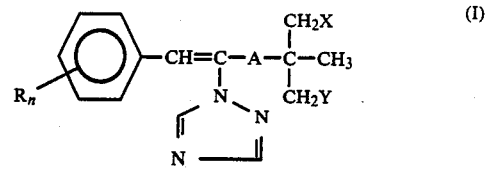

| $R_n$ | A | X | Y |
|---|---|---|---|
| 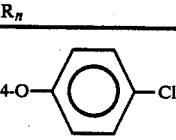 | CH(OH) | H | F |
| 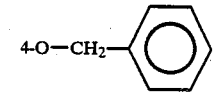 | CH(OH) | H | F |
| 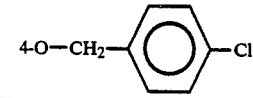 | CH(OH) | H | F |

If, for example, chloropinacolyl-1,2,4-triazole and 4-chlorobenzaldehyde are used as starting substances, the course of the process according to the invention is illustrated by the following equation:

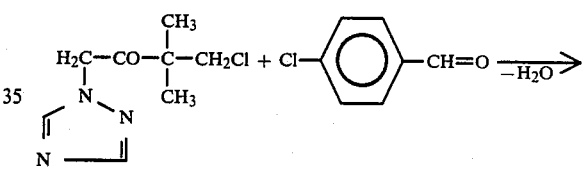

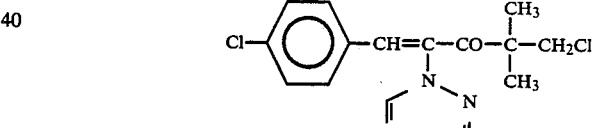

If, for example, 1-chloro-5-(4-chlorophenyl)-2,2-dimethyl-4-(1,2,4-triazol-1-yl)-4-penten-3-one and sodium borohydride are used as starting substances, the course of the process according to the invention is illustrated by the following equation:

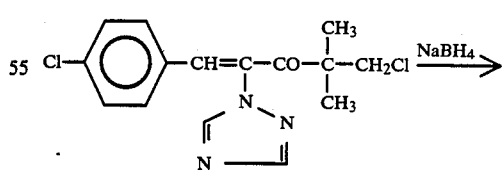

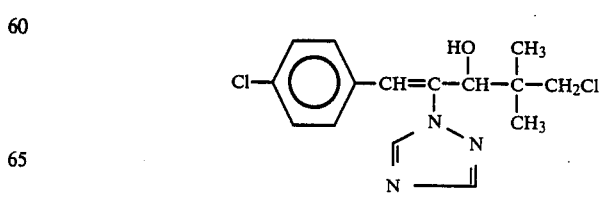

Preferred triazolyl-ketones of formula (II) required as starting substances in carrying out the process according to the invention are those in which X and Y represent those radicals which have already been mentioned for these substituents in connection with the description of the preferred and particularly preferred compounds of the present invention.

The triazolyl-ketones of the formula (II) are known (see DE-OS (German Published Specification) No. 2,820,361), or they can be synthesised by known processes. Thus triazolyl-ketones of the formula (II) are obtained, for example, by a process in which a halogenoketone of the general formula

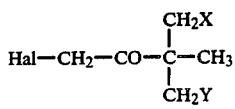

in which
X and Y have the abovementioned meaning and
Hal represents a chlorine or bromine atom,
is reacted with 1,2,4-triazole in the presence of a diluent (such as acetone) and in the presence of an acid-binding agent (such as potassium carbonate) at a temperature between 20° and 150° C.

The halogenoketones of the formula (IV) are known (see, for example, DE-OS (German Published Specification) No. 2,632,603 and DE-OS (German Published Specification) No. 2,843,767), or they are obtained in a generally known manner, by a process in which chlorine or bromine is added to a compound of the formula

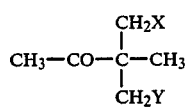

in which X and Y have the abovementioned meaning, in the presence of an inert organic solvent at room temperature; or, for example, a compound of the formula (V) is reacted with a customary chlorinating agent (such as sulphuryl chloride) at a temperature between 20° and 60° C.

Preferred aldehydes of formula (III) also to be used as starting substances for the process according to the invention, are those in which R and n have those meanings which have already been mentioned in connection with the description of the preferred and particularly preferred compounds of the present invention.

The aldehydes of the formula (III) are generally known compounds of organic chemistry.

Preferred possible solvents for the process according to the invention are inert organic solvent. These include, preferably, alcohols (such as methanol and ethanol); ethers (such as tetrahydrofuran and dioxane); aliphatic and cycloaliphatic hydrocarbons (such as hexane and cyclohexane); aromatic hydrocarbons, (such as benzene, toluene and cumene); and halogenated aliphatic and aromatic hydrocarbons (such as methylene chloride, carbon tetrachloride, chloroform, chlorobenzene and dichlorobenzene).

The process according to the invention is carried out in the presence of a catalyst. It is possible to use any of the acid and, in particular, basic catalysts which can customarily be used, as well as buffer mixtures thereof. These include, preferably, Lewis acids (such as boron trifluoride, boron trichloride, tin tetrachloride or titanium tetrachloride); organic bases (such as pyridine and piperidine); and, especially, piperidine acetate.

The reaction temperatures can be varied within a substantial range in carrying out the process according to the invention. In general, the reaction is carried out at a temperature between 20° and 160° C., preferably at the boiling point of the particular solvent.

In carrying out the process according to the invention, 1 to 1.5 moles of aldehyde of the formula (III) and catalytic to 0.2 molar amounts of catalyst are employed per mole of triazolyl-ketone of the formula (II). The end products of the formula (I) are preferentially obtained as E/Z-isomer mixtures.

It is possible to separate the mixture into the pure isomers in the customary manner, for example by crystallisation or by chromatographic separation processes.

The reduction according to the invention is carried out in the customary manner, for example by reaction with complex hydrides, if appropriate in the presence of a diluent, or by reaction with aluminium isopropylate in the in the presence of a diluent.

If complex hydrides are used, possible diluents for the reaction according to the invention are polar organic solvents. These include, preferably, alcohols (such as methanol, ethanol, butanol and isopropanol), and ethers (such as diethyl ether or tetrahydrofuran). The reaction is in general carried out at a temperature between −10° and +30° C., preferably at a temperature between −10° and 20° C. For this reaction, about 1 mole of a complex hydride, such as sodium borohydride, calcium borohydride or lithium alanate, is employed per mole of the ketone of the formula (Ia).

To isolate the reduced compounds of the formula (I), the residue is taken up in dilute hydrochloric acid and the mixture is then rendered alkaline and extracted with an organic solvent. Further working up is effected in the customary manner, as is any separation of the E/Z-isomer mixture.

If aluminium isopropylate is used, preferred possible diluents for the reaction according to the invention are alcohols (such as isopropanol), or inert hydrocarbons (such as benzene). The reaction temperatures can again be varied within a substantial range; in general, the reaction is carried out at a temperature between 20° and 120° C., preferably at a temperature between 50° and 100° C. For carrying out the reaction, about 1 to 2 moles of aluminium isopropylate are employed per mole of the appropriate ketone of the formula (Ia). To isolate the reduced compounds of the formula (I), the excess solvent is removed by distillation in vacuo and the aluminium compound formed is decomposed with dilute sulphuric acid or sodium hydroxide solution. Further working up is effected in the customary manner. Exclusively the Z-isomers are obtained in the reduction with aluminium isopropylate.

An unambiguous characterising feature for the two geometric isomers is the $H^1$-nuclear magnetic resonance of the two triazole protons. The difference between the shift values of these two protons in the E-forms is approximately twice the difference in the corresponding Z-forms.

The following acids can preferably be used for the preparation of physiologically acceptable acid addition salts of the compounds of the formula (I): the hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as, acetic acid, maleic acid, succinic acid, fumaric acid, tartaric acid, citric acid, salicylic acid, sorbic acid and lactic acid), and sulphonic acids (such as, for example, p-toluenesulphoni acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII of the periodic table can preferably be used for the preparation of metal salt complexes of the compounds of the formula (I), examples of metals which may be mentioned being copper, zinc, manganese, magnesium, tin, iron and nickel.

Possible anions of the salts are, preferably, those which are derived from the following acids: hydrogen halide acids (such as hydrochloric acid and hydrobromic acid, phosphoric acid and sulphuric acid.

The metal salt complexes of compounds of the formula (I) can be obtained in a simple manner by customary processes, thus, for example, by dissolving the metal salt in alcohol (for example ethanol), and adding the solution to the compound of the formula (I). The metal salt complexes can be purified in a known manner, for example by filtration, isolation and, if appropriate, by recrystallisation.

The active compounds according to the invention engate in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants in connection also with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest of facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants for example pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of growth regulators depends on the climate and vegetative circumstances.

The foregoing description should not be taken as implying that each of the compounds can exhibit all of the desired effect on plants. The effect exhibited by a compound in any particular set of circumstances must be determined empirically.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds at the concentrations required for combating plant diseases permits treatment of above-ground parts of plants, of vegetative propagation stock and seeds, and of the soil.

As plant protection agents, the active compounds according to the invention can be used with particularly good success for combating those fungi which cause powdery mildew diseases; thus, for combating Erysiphe species, such as, for example, against the powdery mildew or barley or cereal causative organism (*Erysiphe graminis*) and the powdery mildew of cucumber causative organism (*Erysiphe cichoracearum*); and for combating *Pyricularia oryzae* and *Pellicularia sasakii*. It should be particularly emphasised that the active compounds according to the invention not only display a protective action but also have a systemic action. Thus, it is possible to protect plants from fungal attack if the active compound is fed to the above-ground parts of the plant via the soil and the root or via the seed.

When applied in appropriate amounts, the compounds according to the invention also exhibit a herbicidal action.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well a their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be use crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellants, growth factors, plant nutrients, agents for improving soil structure and plant growth regulators.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporising, injecting, forming a slurry, brushing on, dusting, scattering, dry dressing, moist dressing, wet dressing, slurry dressing or encrusting. It is furthermore possible to apply the active compounds in accordance with the ultra-low volume process or to inject the active compound preparation or the active compound itself into the soil. It is also possible to treat the seeds of the plants.

When the compounds according to the invention are used as plant growth regulators, the amounts applied can be varied within a substantial range. In general, 0.01 to 50 kg, preferably 0.05 to 10 kg, of active compound are employed per hectare of soil surface.

The amount applied can also be varied within a substantial range, depending on the type of application, when the substances according to the invention are used as fungicides. Thus, especially in the treatment of parts of plants, the active compound concentrations in the use forms are in general between 1 and 0.0001% by weight, preferably between 0.5 and 0.001% by weight. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

The present invention also provides plant growth regulation and fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present-invention was applied alone or in admixture with a diluent or carrier.

It will be seen that the usual methods of providing a harvested crop may be improved by the present invention.

PREPARATIVE EXAMPLES

EXAMPLE 1

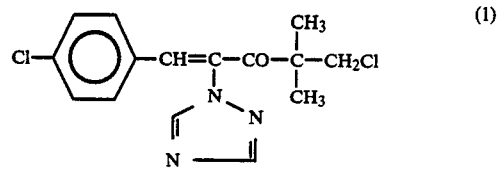

E/Z-isomer mixture

EXAMPLE 2

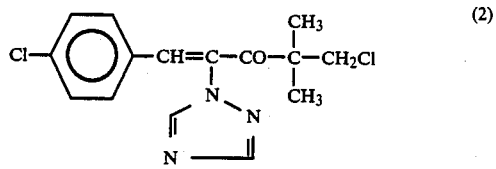

E-isomer 201.5 g (1 mole) of 1-chloro-2,2-dimethyl-4-(1,2,4-triazol-1-yl)-butan-3-one, 140.5 g (1 mole) of 4-chlorobenzaldehyde, 9,9 ml of piperidine and 30 g of glacial acetic acid in 300 ml of toluene were heated under reflux for 8 hours, the water of reaction formed being removed azeotropically. The reaction mixture was then washed with water and with dilute sodium bicarbonate solution, dried over sodium sulphate and evaporated in vacuo. 305.9 (94.4% of theory) of crude 1-chloro-5-(4-chlorophenyl)-2,2-dimethyl-4-(1,2,4-triazol-1-yl)-4-penten-3-one of boiling point 165° C./0.1 mm Hg were obtained as the E/Z-isomer mixture. The E-isomer could be isolated as crystals by stirring the product with isopropanol or ethanol. The E-isomer had a melting point of 112° C.

Preparation of the starting material

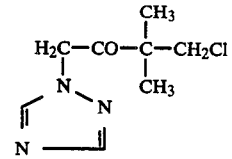

43.3 g (0.32 mole) of 1-chloro-2,2-dimethyl-butan-2-one were dissolved in 250 ml of ether and 52 g (0.325 mole) of bromine were added dropwise at 20° C., whilst cooling. The mixture was subsequently stirred for 1 hour, and the ethereal solution was washed five times with 100 ml of water each time, dried over sodium sulphate and concentrated in vacuo. The resulting 4-bromo-1-chloro-2,2-dimethyl-butan-2-one was taken up in 50 ml of acetone and the mixture was added dropwise to a mixture of 23.1 g (0.33 mole) of 1,2,4-triazole and 46.2 g (0.4 mole) of potassium carbonate in 250 ml of acetone at room temperature, whilst cooling. The mixture was subsequently stirred at 20° C. for 4 hours, the inorganic precipitate was filtered off and the filtrate was concentrated in vacuo. 57.9 g (90% of theory) of 1-chloro-2,2-dimethyl-4-(1,2,4-triazol-1-yl)-butan-2-one, which could be further reacted directly, were obtained.

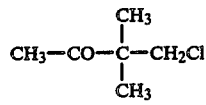

11.6 g (0.1 mole) of 2,2-dimethyl-1-hydroxy-butan-3-one were added dropwise to 20.5 g (0.1 mole) of N,N-diethyl-1,2,2-trichlorovinyl-amine at 50° to 60° C. (cooling with ice). After stirring the mixture at 60° C. for two hours, it was distilled under a waterpump vacuum. 8.1 g (60% of theory) of 1-chloro-2,2-dimethyl-butan-3-one of boiling point 60°–62° C./12 mm Hg were obtained.

(1-Chloro-2,2-dimethyl-butan-3-one was obtained in a yield of 90% when equimolar amounts of 2,2-dimethyl-1-hydroxy-butan-3-one and triphenylphosphine were heated under reflux in ten times the amount of carbon tetrachloride for 12 hours, the solvent was distilled off, the residue was taken up in ether, the mixture was filtered and the filtrate was distilled).

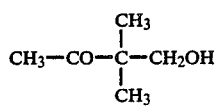

66 g (2.2 moles) of paraformaldehyde and 1 g of potassium hydroxide in 10 ml of methanol were added dropwise to 172 g (2 moles) of methyl isopropyl ketone in 1,000 ml of methanol. The mixture was heated under reflux for 15 hours and the methanol was then distilled off over a column, at an internal temperature of 82° C. The residue was distilled under a waterpump vacuum. 152.7 g (68% of theory) of 2,2-dimethyl-1-hydroxy-butan-3-one of boiling point 80°–82° C./12 mm Hg were obtained.

EXAMPLE 3

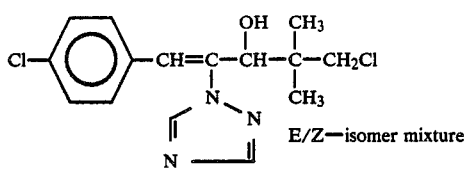

162 g (0.5 mole) of 1-chloro-5-(4-chlorophenyl)-2,2-dimethyl-4-(1,2,4-triazol-1-yl)-4-penten-3-one (obtained as described in Example 1) were dissolved in 500 ml of isopropanol, and 9.5 g (0.25 mole) of sodium borohydride were added in portions, whilst stirring. The reaction mixture was stirred at room temperature for 10 hours and then concentrated in vacuo. The residue was taken up in toluene, washed with dilute acetic acid and then with water, dried over sodium sulphate and concentrated in vacuo. 156.6 g (96% of theory) of 1-chloro-5-(4-chlorophenyl)-2,2-dimethyl-4-(1,2,4-triazol-1-yl)-4-penten-3-ol with a refractive index $n_D^{20}$ of 1.5579 were obtained as an E/Z-isomer mixture.

EXAMPLE 4

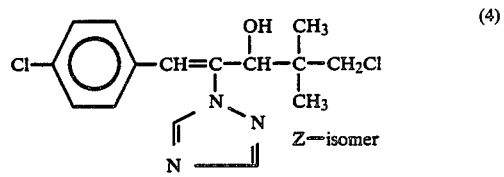

48.6 g (0.15 mole) of 1-chloro-5-(4-chlorophenyl)-2,2-dimethyl-4-(1,2,4-triazol-1-yl)-4-penten-3-one (prepared as described in Example 1) and 30.6 g (0.15 mole) of aluminium isopropylate in 200 ml of isopropanol were heated under reflux for 7 hours, isopropanol and acetone being continuously distilled off over a 30 cm Vigreux column until acetone could no longer be detected in the distillate. The reaction mixture was then concentrated and ice/hydrochloric acid was added to the residue. The mixture was extracted with methylene chloride. The combined methylene chloride extracts were dried over sodium sulphate and concentrated in vacuo. The oily residue was subjected to separation by column chromatography (silica gel/chloroform). The non-reduced E-isomer of 1-chloro-5-(4-chlorophenyl)-2,2-dimethyl-4-(1,2,4-triazol-1-yl)-penten-3-one (the compound of Example 2) and pure 1-chloro-5-(4-chlorophenyl)-2,2-dimethyl-4-(1,2,4-triazol-1-yl)-penten-3-ol of melting point 120° C., as the Z-isomer, were obtained.

EXAMPLE 5

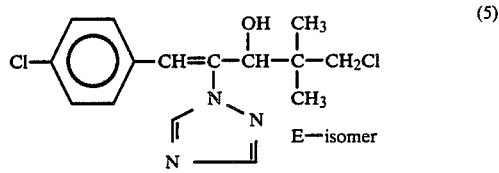

2.0 g (6.13 moles) of the E-isomer of 1-chloro-5-(4-chlorophenyl)-2,2-dimethyl-4-(1,2,4-triazol-1-yl)-4-penten-3-one (the compound of Example 2) and 0.467 g (4.11 mmoles) of calcium chloride were dissolved in 30 ml of isopropanol, and a solution of 0.167 g (4.3 mmoles) of sodium borohydride was added dropwise at −5° C. After 6 hours, the reaction mixture was warmed to 25° C. and concentrated in vacuo. The residue was poured onto water and the mixture was extracted with ethyl acetate. The combined ethyl acetate extracts were dried over sodium sulphate and concentrated in vacuo. The oily residue crystallised on trituration with diisopropyl ether. 1.1 g (55% of theory) of 1-chloro-5-(4-chlorophenyl)-2,2-dimethyl-4-(1,2,4-triazol-1-yl)-4-penten-3-ol of melting point 170° C. were obtained as the E-isomer.

The following compounds of the general formula (I) were obtained in a corresponding manner:

TABLE 2

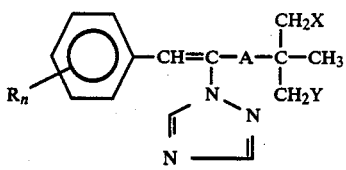

| Example No. | $R_n$ | A | X | Y | Melting point (°C.) or refractive index $n_D^{20}$ |
|---|---|---|---|---|---|
| 6 | 4-Cl | CO | H | F | 1,5672 |
| 7 | 4-C(CH₃)₃ | CO | H | F | 1,5565 |
| 8 | 4-C(CH₃)₃ | CO | H | Cl | 1,5655(Z-Isomer) |
| 9 | 4-N(CH₃)₂ | CO | H | F | 100 |
| 10 | 4-N(CH₃)₂ | CO | H | Cl | 84 |
| 11 | 2-Cl | CO | H | F | 1,5632(E-Isomer) |
| 12 | 4-Cl | CH(OH) | H | F | 230(×NDS) |
| 13 | 4-Cl | CH(OH) | H | F | 110(Z-Isomer) |
| 14 | 4-C(CH₃)₃ | CH(OH) | H | F | 1,5250 |
| 15 | 4-C(CH₃)₃ | CH(OH) | H | F | 1,5820(Z-Isomer) |
| 16 | 4-N(CH₃)₂ | CH(OH) | H | F | 118(Z-Isomer) |
| 17 | 4-N(CH₃)₂ | CH(OH) | H | Cl | 120(Z-Isomer) |
| 18 | 2-Cl | CH(OH) | H | F | 116(Z-Isomer) |
| 19 | 2-Cl | CH(OH) | H | F | 140(E-Isomer) |
| 20 | 4-OCF₃ | CH(OH) | H | Cl | 100(Z-Isomer) |
| 21 | 4-OCF₃ | CH(OH) | H | Cl | 140(E-Isomer) |
| 22 | 2,4-Cl₂ | CH(OH) | H | F | 150(Z-Isomer) |
| 23 | 2,4-Cl₂ | CH(OH) | H | F | 158(E-Isomer) |
| 24 | 4-Cl | CO | F | F | 1,5728 |
| 25 | 2,4-Cl₂ | CO | F | F | 1,5778 |
| 26 | 4-Cl | CO | Cl | Cl | 1,5942 |
| 27 | 2,4-Cl₂ | CO | Cl | Cl | 1,5868 |
| 28 | 4-Cl | CH(OH) | F | F | 74(E-Isomer) |
| 29 | 4-Cl | CH(OH) | F | F | 110(Z-Isomer) |
| 30 | 2,4-Cl₂ | CH(OH) | F | F | 157(E-Isomer) |
| 31 | 2,4-Cl₂ | CH(OH) | F | F | 154(Z-Isomer) |
| 32 | 4-Cl | CH(OH) | Cl | Cl | 150(Z-Isomer) |
| 33 | 2,4-Cl₂ | CH(OH) | Cl | Cl | 148(Z-Isomer) |
| 34 | 4-Cl | CH(OH) | H | F | 88(E-Isomer) |
| 35 | 4-F | CH(OH) | H | Cl | 122(Z-Isomer) |
| 36 | 4-F | CH(OH) | H | Cl | 150(E-Isomer) |
| 37 | 4-F | CH(OH) | H | F | 108(Z-Isomer) |
| 38 | 4-Cl | CH(OH) | H | F | 1,5421 |
| 39 | 2,4-Cl₂ | CH(OH) | H | Cl | 150(Z-Isomer) |
| 40 | 2,4-Cl₂ | CH(OH) | H | Cl | 140(E-Isomer) |
| 41 | 4-F | CO | H | Cl | 58(E-Isomer) |
| 42 | 2,4-Cl₂ | CO | H | F | oil(E-Isomer) |

NDS = 1,5-naphthalenedisulphonic acid

The plant growth regulation and fungicidal activity of the compounds of this invention is illustrated by the following biotest Examples.

In these Examples, the compounds according to the present invention are each identified by the number (given in brackets) of the corresponding preparative Example, which will be found earlier in this specification.

The known comparison compounds are identified as follows:

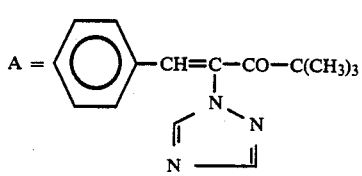

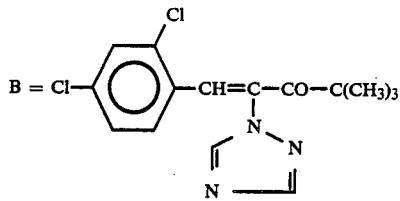

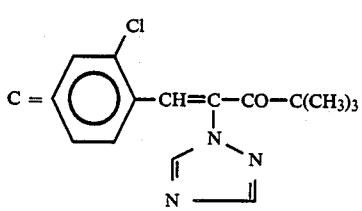

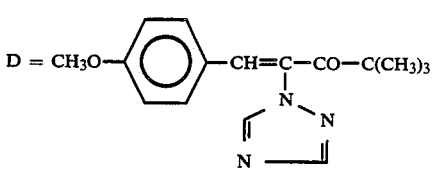

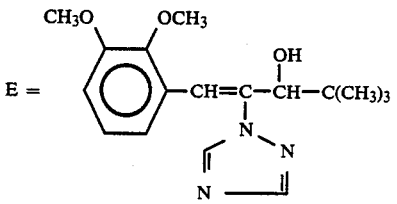

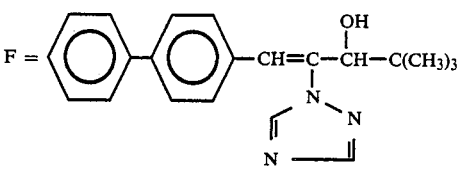

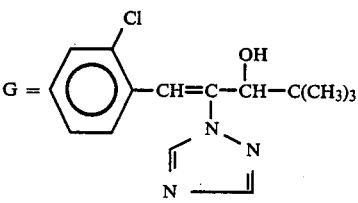

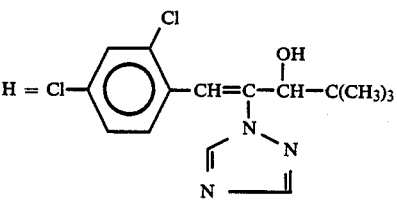

EXAMPLE A

Inhibition of growth of soya beans

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

In this test, a very significantly superior activity compared with the compounds (A), (B), (D), (E), (F) and (G) known from the prior art was shown, for example, by the compounds (3), (4), (7), (12), (13), (14), (35), (36), (37), (38), (40).

EXAMPLE B

Inhibition of growth of cotton

Solvent: 30 parts by weight of dimethylformamide
Emulsifier: 1 part by weight of polyoxyethylene sorbitane monolaurate To produce a suitable preparation of active compound 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in percent of the additional growth of the control plants was calculated. 100% inhibition of growth meant that growth had stopped and 0% denoted a growth corresponding to that of the control plants.

In this test, a very significantly superior activity compared with the compounds (A), (B), (E), (F), and (H) known from the prior art was shown, for example, by the compounds (3), (4), (7), (13), (14), (36), (37), (38), (40).

EXAMPLE C

Inhibition of growth of sugar beet

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the inhibition of growth in percent of the additional growth of the control plants was calculated. 0% inhibition of growth denoted a growth which corresponded to that of the control plants. 100% inhibition of growth meant that growth had stopped.

In this test, active compounds (3), (4), (12), (13), (35), (36), (37), (38), (39), (40) showed a better inhibition of growth than the compounds (E) and (F) known from the prior art.

EXAMPLE D

Resistance to dryness of sugar beet

When young sugar beet plants were treated with the active compound preparation, a resistance towards soil dryness was found, especially with compound (3) in concentrations of 250 and 125 ppm.

EXAMPLE E

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f. sp. hordei.*

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with the compounds (B) and (E) known from the prior art was shown, for example, by the compounds (6), (7), (3), (4), (12), (13) and (14).

EXAMPLE F

Powdery mildew of barley test (*Erysiphe graminis var. hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had unfolded their first leaf, they were dusted with fresh spores of *Erysiphe graminis var. hordei* and grown on at 21° to 22° C. and 80 to 90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active was the active compound, the lower was the degree of mildew infection.

In this test, a significantly superior activity compared with the compound (H) known from the prior art was shown, for example, by the compound (3).

EXAMPLE G

Erysiphe test (cucumbers)/protective
Solvent: 4.7 parts by weight of acetone
Emulsifier: 0.3 part by weight of alkylaryl polyglycol ether
Water: 95.0 parts by weight.

The amount of the active compound required for the desired concentration of active compound in the spray liquid was mixed with the stated amount of solvent and the concentrate was diluted with the stated amount of water which contained the stated additions.

Young cucumber plants with about three foliage leaves were sprayed with the spray liquid until dripping wet. The cucumber plants remained in a greenhouse for 24 hours to dry. They were then for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% denoted that the plants were totally infected.

In this test, for example, the following compounds showed a very good action which was superior to that of the compounds (D) and (E) known from the prior art: (6), (7), (14), (2) and (13).

It will be understood that the specification and examples are illustrative but not limitative of the present invention and that other embodiments within the spirit and scope of the invention will suggest themselves to those skilled in the art.

What is claimed is:

1. Halogenated triazolylvinyl carbinol compound of the formula

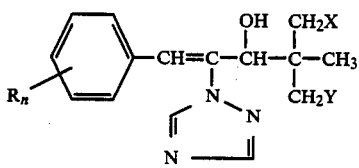

wherein
X is hydrogen, and
Y is fluorine or chlorine; or X and Y are identical and are fluorine or chlorine;
$R_n$ is 4-chloro, 2,4-dichloro, 4-tert.-butyl, 4-methoxy or 4-trifluoromethoxy, or
a physiologically acceptable acid addition salt thereof with 1,5-naphthalenedisulphonic acid.

2. Compound as claimed in claim 1, wherein X is hydrogen.
3. Compound as claimed in claim 1 wherein X is fluorine or chlorine.
4. Compound as claimed in claim 1 wherein R is tert.-butyl.
5. Compound as claimed in claim 1 wherein R is methoxy.
6. Compound as claimed in claim 1 wherein R is trifluoromethoxy.
7. Compound as claimed in claim 1, wherein $R_n$ is 4-chloro.
8. Compound as claimed in claim 1, wherein $R_n$ is 2,4-dichloro.
9. Compound as claimed in claim 1, wherein said compound is designated 2-methyl-2-fluoromethyl-4-(1,2,4-triazol-1-yl)-5-(4-chlorophenyl)-4-penten-3-ol.
10. Fungicidal composition containing, as an active ingredient, 0.1 to 95% by weight of a compound as claimed in claim 1 in admixture with an agriculturally acceptable carrier.
11. Method of combating fungi, wherein there is applied to the fungi, or to the habitat thereof, an effective amount of a triazolylvinyl carbinol compound as claimed in claim 1.
12. Composition as claimed in claim 10, containing 1 to 0.0001% of the active compound by weight.
13. Composition as claimed in claim 10, containing 0.5 to 0.001% of the active compound by weight.
14. Plant growth regulant composition containing, as an active ingredient, 0.1 to 95% by weight of a compound as claimed in claim 1 in admixture with an agriculturally acceptable carrier.
15. Plant growth regulant composition containing, as an active ingredient, 0.1 to 95% by weight of a compound as claimed in claim 1 admixture with a liquid diluent or carrier containing a surface-active agent.
16. Method of regulating plant growth, wherein there is applied to the plants, or to the habitat thereof, an effective amount of a triazolylvinyl carbinol compound as claimed in claim 1.
17. Plant growth regulant composition as claimed in claim 15, containing 1 to 0.0001% of the active compound by weight.
18. Plant grwoth regulant composition as claimed in claim 15, containing 0.5 to 0.001% of the active compound by weight.
19. A method of regulating plant growth as claim in claim 16, wherein said active compound is applied in an amount of 0.1 to 50 kg per hectare.
20. A method of regulating plant growth as claimed in claim 16, wherein said active compound is applied in an amount of 0.05 to 10 kg per hectare.

* * * * *